United States Patent [19]
Ward

[11] Patent Number: 4,907,969
[45] Date of Patent: Mar. 13, 1990

[54] UNIVERSAL DENTAL PROSTHESIS RETENTION SYSTEM

[76] Inventor: Whitley S. Ward, 2171 Forest La., Naples, Fla. 33940

[21] Appl. No.: 181,517

[22] Filed: Apr. 14, 1988

[51] Int. Cl.⁴ ............................................... A61C 8/00
[52] U.S. Cl. ..................................... 433/173; 433/174
[58] Field of Search ............... 433/173, 174, 177, 220, 433/221, 169, 193, 194, 196

[56] References Cited

U.S. PATENT DOCUMENTS

| | | | |
|---|---|---|---|
| 1,193,329 | 8/1916 | Witbycombe | 433/169 |
| 2,303,874 | 12/1942 | Brown | 433/194 |
| 3,732,621 | 5/1973 | Bostrom | 433/174 |
| 3,808,606 | 5/1984 | Tronzo | 433/173 X |
| 4,488,875 | 12/1984 | Niznick | 433/173 |
| 4,518,357 | 5/1985 | Brinkmann et al. | 433/173 |
| 4,604,060 | 8/1986 | Weissman | 433/221 |
| 4,626,213 | 12/1986 | Shiner et al. | 433/173 |
| 4,713,004 | 12/1987 | Linkow et al. | 433/174 |
| 4,793,808 | 12/1988 | Kirsch | 433/173 |
| 4,854,872 | 8/1989 | Detsch | 433/174X |

FOREIGN PATENT DOCUMENTS 8414  2/1907  France .................................. 433/221

Primary Examiner—Robert P. Swiatek
Assistant Examiner—Nicholas D. Lucchesi
Attorney, Agent, or Firm—Charles J. Prescott

[57] ABSTRACT

A universal dental prosthesis retention system adapted to interconnect a dental implant secured in a patient's jaw bone to an artificial dental prosthesis. The retention system includes an implant insert having a first longitudinal axis and securable into the dental implant, a prosthesis insert having a second longitudinal axis and securable within the dental prosthesis, and a universal connector adapted to interconnect the implant insert and prosthesis insert. The universal connector is also adapted to facilitate preselected or adjustable universal angular alignment between the first and second axes, that angular relationship then securably lockable to enable the dental prosthesis to be thereafter securely mounted over the prosthesis insert. Various locking structures and universal connector structure are provided.

7 Claims, 3 Drawing Sheets

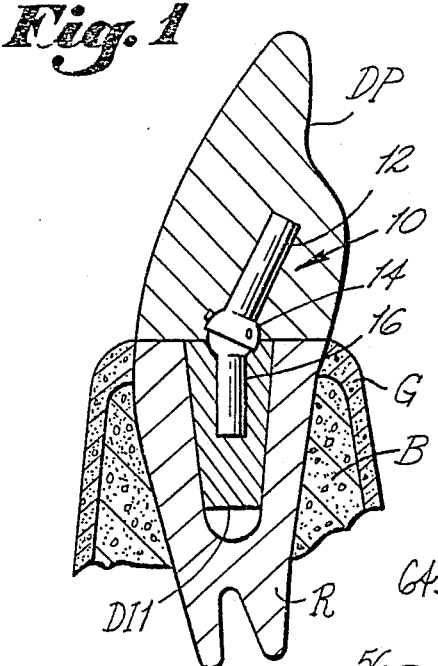
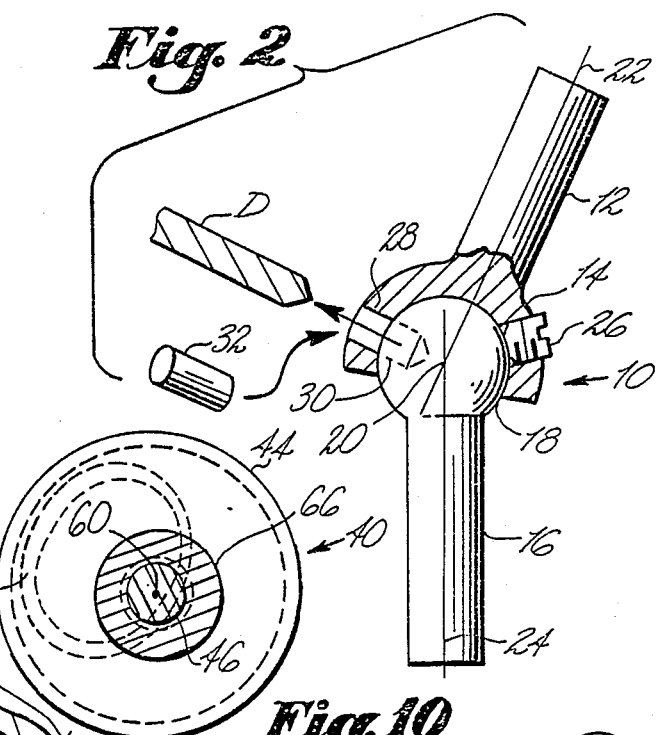
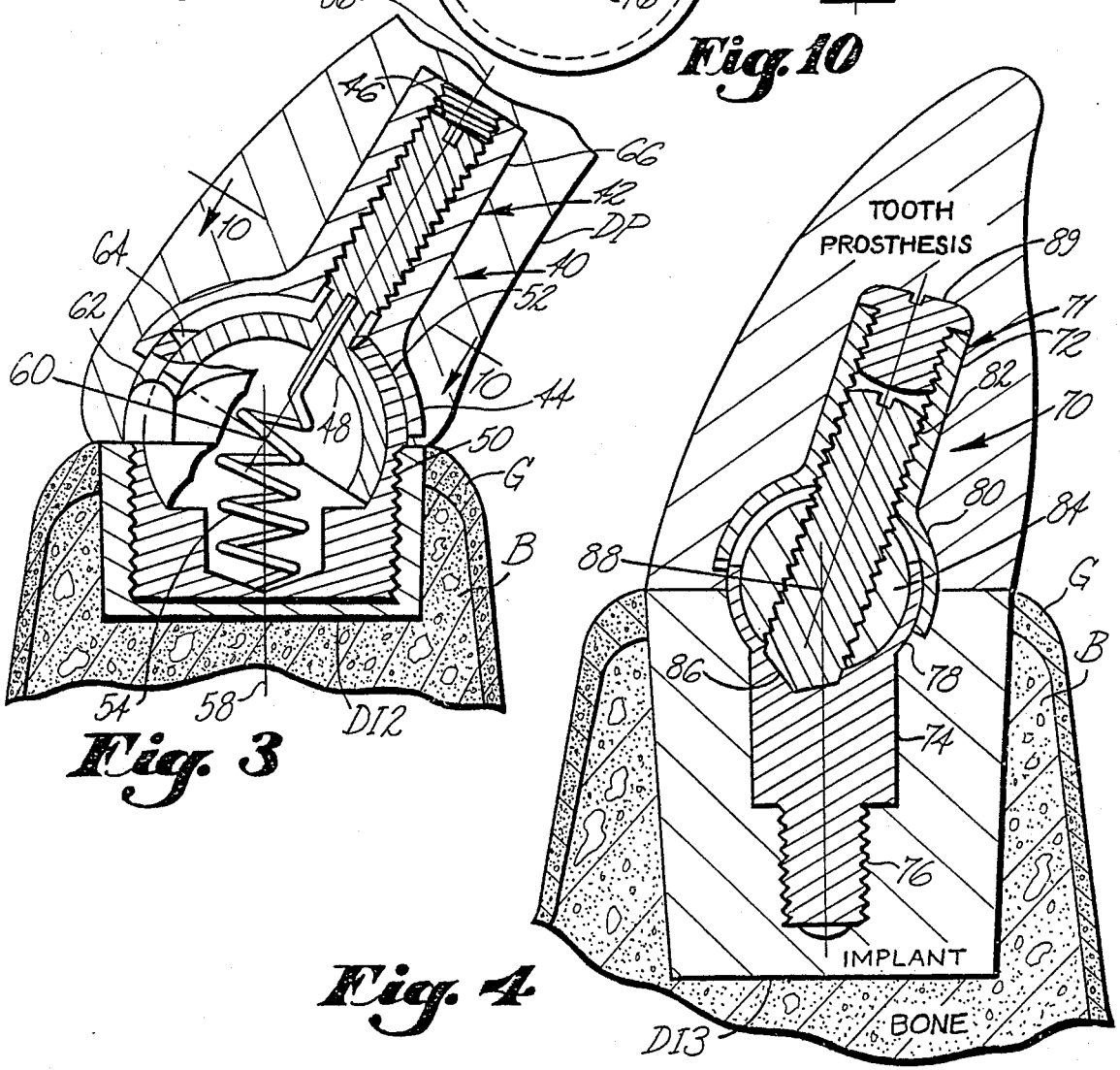

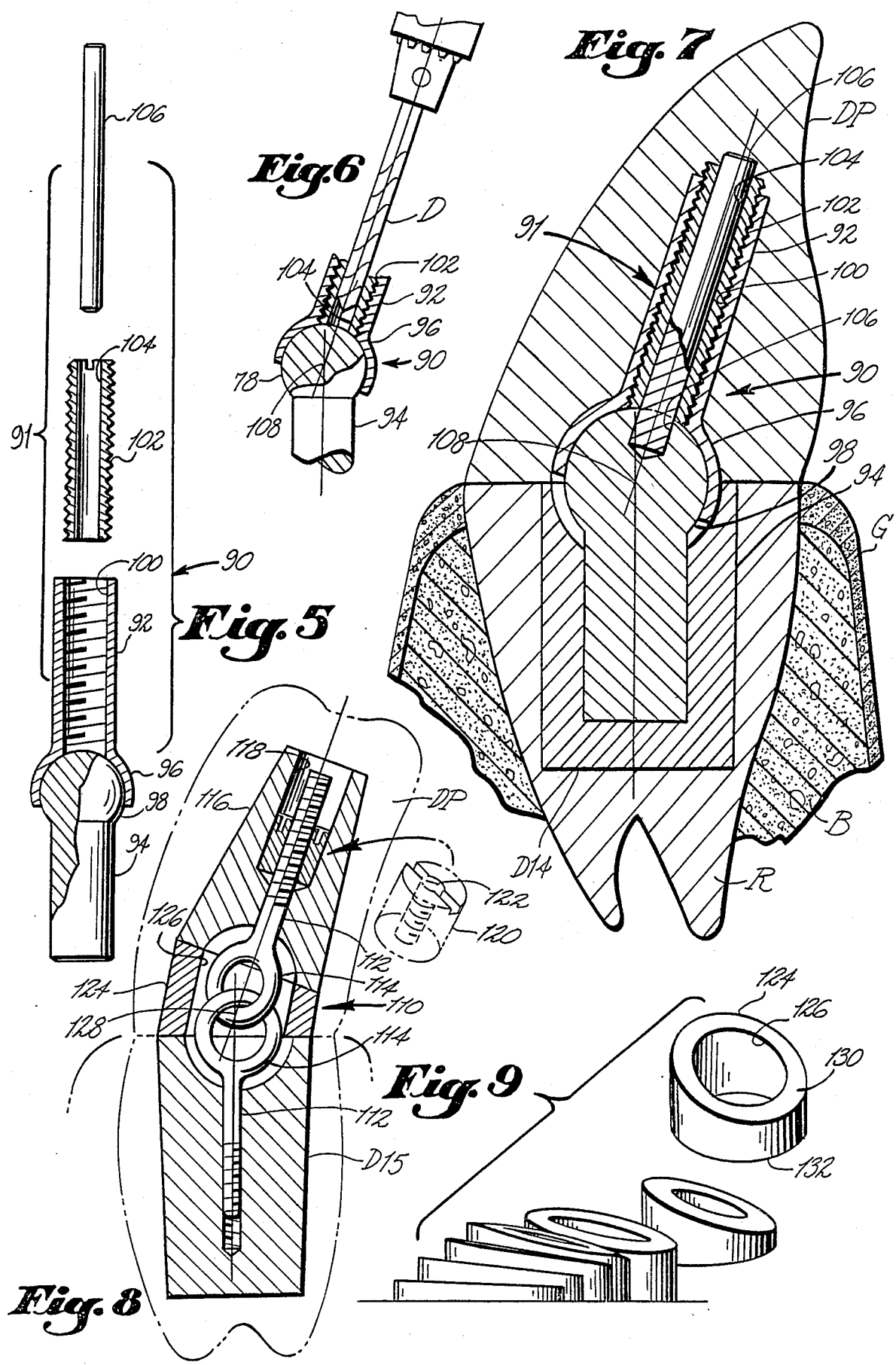

UNIVERSAL DENTAL PROSTHESIS RETENTION SYSTEM

BACKGROUND OF THE INVENTION

The present invention relates generally to dental implants and to the replacement of removed or broken teeth with artificial dental prostheses, and more particularly to the interconnection and adjustable alignment between the artificial dental implant and a dental prosthesis.

Whenever a natural tooth is lost, it is often possible to surgically implant an artificial replacement for the root of the lost tooth into the jawbone. These devices are commonly called dental implants. The function of these dental implants is to provide support for an artificial tooth or dental prosthesis, the implant thus functioning as an artificial root. Various devices are available to interconnect such implants with a dental prosthesis or an artificial tooth. Such interconnecting devices are commonly called dental implant inserts. These implant inserts are affixed into and extend upwardly from the dental implant that would normally protrude above the gum tissue into the oral cavity. Most modern dental implants are first surgically placed into the jawbone and, after a period of four to six months for healing, the implant insert is affixed to the dental implant. This allows the dental practitioner to be confident that the bony tissues have "osseointegrated" to the implant which is necessary for the biological success of the implant. At this time, an implant insert is attached to the dental implant by either threading engagement or cementation.

However, where a portion of the tooth remains within the jawbone, a cavity is prepared in the remaining tooth into which a suitable dental implant is embedded and secured.

A number of such dental implants are known to applicant as follows:

| | |
|---|---|
| #4,252,525 | Child |
| #4,671,768 | Ton |
| #4,270,905 | Mohammed |
| #4,195,409 | Child |
| #3,797,113 | Brainin |
| #3,717,932 | Brainin |
| #3,629,943 | Gindea |

Two additional unpatented dental implants, typically, are known to applicant and distributed by Whaledent, International under their trademarks TRIAX and PARA POST PLUS.

Additionally, artificial dentures or prostheses have been patented as disclosed in U.S. Pat. No. 3,343,262 to Burg and in U.S. Pat. No. 4,318,696 to Casama.

Implant inserts presently available, however, do not adequately address certain problems associated with fabrication of artificial teeth and/or a dental prosthesis associated with dental implants. With regard to dental prostheses, ideally, dental implants and their associated implants insert should be positioned parallel with adjacent natural teeth and also positioned parallel with other implants that may be required. Unfortunately, such needed parallelism is often difficult to attain because of anatomical considerations within the jawbone, loss of excess bone, and a common presence of misaligned natural teeth. As a result of these conditions, it is often desirable for the dental practitioner to be able to vary the angle between the implant axis of the dental insert and that of the dental insert, thus achieving needed parallelism. It is therefore extremely useful that the dental practitioner have the ability to easily vary this angular relationship between the implant and the implant insert at the time that the implant insert is attached to the previously permanently secured and positioned dental implant.

Two methods of attaching an implant insert to a permanently secured dental implant are presently available. The first is by cementation of the implant insert into the implant while the second method is by threadable engagement of the implant insert within the implant. The only method known to applicant, a practicing dentist (D.D.S.), for accommodating misaligned installation of the implant insert dental prostheses is to individually fabricate the interconnecting structure between dental implant and dental prosthesis or to substantially deform presently available means for interconnecting these two components prior to, or after, installation into the dental implant.

A further difficulty with regard to threaded implant inserts is that, if the dental practitioner must manually modify it to accommodate angular misalignment, it is extremely difficult to determine the exact rotational relationship between the implant and the implant insert when they are secured tightly together unless the final rotational relationship is established prior to deforming the implant insert or fabricating a custom implant insert.

It is here emphasized that, throughout this disclosure, the term "dental implant" or "implant" includes those devices which are securable within the remaining root portion of a tooth, as well as those devices which are intended to fully replace all tooth root material and to be "osseointegranted" into the jawbone. Therefore, my invention is equally applicable to both types of implants.

The present invention provides a universal dental prosthesis retention system which conveniently allows the dental practitioner to universally adjust the angular misalignment between the longitudinal axes of the dental implant and the implant insert and, thereafter, to securely lock this nonaligned arrangement for receipt of the dental prosthesis atop the prosthesis insert portion of the invention.

BRIEF SUMMARY OF THE INVENTION

This invention is directed to a universal dental prosthesis retention system adapted to interconnect a dental implant secured in a patient's jaw bone to an artificial dental prosthesis. The retention system includes an implant insert having a first longitudinal axis and securable into the dental implant, a prosthesis insert having a second longitudinal axis and securable within the dental prosthesis, and a universal connector adapted to interconnect the implant insert and prosthesis insert. The universal connector is also adapted to facilitate preselected or adjustable universal angular alignment between the first and second axes, that angular relationship then securably lockable to enable the dental prosthesis to be thereafter securely mounted over the prosthesis insert. Various locking means and universal connector means are provided.

It is therefore an object of this invention to provide a universal dental prosthesis retention system for the interconnection of a dental implant with a nonaligned dental prosthesis.

It is another object of this invention to provide a universally adjustable dental prosthesis retention system for the adjustable axial alignment and the secure connection of a dental prosthesis to a dental implant.

It is yet another object of the present invention to provide an incrementally adjustable dental prosthesis retention system for the adjustable axial alignment and the secure connection of a dental prosthesis to a dental implant.

It is yet another object of the above invention to be adaptable to existing dental implants and dental prostheses.

In accordance with these and other objects which will become apparent hereinafter, the instant invention will now be described with reference to the accompanying drawings in which:

BRIEF DESCRIPTION OF THE DRAWINGS

FIG. 1 is a side elevation section view of one embodiment of the invention in place between a dental implant in the tooth root and a dental prosthesis.

FIG. 2 is an enlarged broken section view of the invention shown in FIG. 1.

FIG. 3 is a side elevation section view of another embodiment of the invention.

FIG. 4 is a side elevation section view of yet another embodiment of the invention.

FIG. 5 is an exploded partial section view of yet another embodiment of the invention.

FIG. 6 is a partial broken section view depicting the boring of a cavity into the ball of the embodiment shown in FIG. 5.

FIG. 7 is a side elevation section view of the embodiment of the invention shown in FIG. 5 installed.

FIG. 8 is a side elevation section view of yet another embodiment of the invention showing the jawbone, tooth root, and dental prosthesis in phantom.

FIG. 9 is a perspective view of the array of angular spacers utilized in the embodiment shown in FIG. 8.

FIG. 10 is a section view in the direction of arrows 10—10 in FIG. 3.

DETAILED DESCRIPTION OF THE INVENTION

Figure 12:
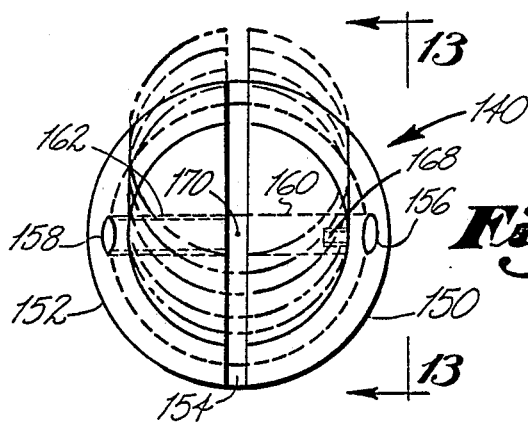
FIG. 12 is a view in the direction of arrows 12—12 in FIG. 11.

Referring now to the drawings, and particularly to FIGS. 1 and 2, one embodiment of the invention is shown generally at 10 and includes a prosthesis insert 12, which is securely engageable within a dental prosthesis DP, and an implant insert 16 which is rigidly securable within a dental implant DI1. Interconnection of the prosthesis insert 12 within the dental prosthesis DP may be by permanent cementation or threadable engagement to facilitate later removal while the interconnection of the implant insert 16 within the dental implant DI1 may be by bonding or by mating threadable engagement.

The implant insert 16 includes an enlarged spherically shaped ball 18 disposed at its upper end which mateably and lockably engages into socket 14 disposed at the lower end of the prosthesis insert 12. Thus, prior to locking, the longitudinal axis 22 of the prosthesis insert 12 may be universally articulated about an imaginary point of articulation 20 formed at the intersection with longitudinal axis 24 of implant insert 16.

In use, once the dental practitioner has determined the appropriate angular orientation of longitudinal axis 22 such that prosthesis insert 12 is generally centered within the mid-portion of dental prosthesis DP without impinging too closely to one of the surfaces of dental prosthesis DP, set screw 26 is provided when tightening to inhibit further movement between socket 14 and ball 18. Virtually complete rigidity between the prosthesis insert 12 and the implant insert 16 may be then established by use of a drill bit D used to drill cavity 30 in alignment and registry with aperture 28 previously formed in socket 14. Thereafter, locking pin 32 is securely fixed by cementation, threadable engagement or interference fit within aperture 28 and cavity 30, being additionally held in that position by the dental prosthesis DP which is to be installed around and encapsulating the prosthesis insert 12.

In this embodiment 10 as depicted in FIG. 1, the dental implant DI1 is shown secured within the root R of the lower part of the patient's tooth which remains normally embedded within the alveolar bone B and gingiva G. However, other embodiments of the invention, including that depicted in FIGS. 1 and 2, are equally well adapted to be interconnected within dental implants which completely replace the root R of the tooth and have been securely engaged by various methods within the alveolar bone B itself.

Referring now to FIGS. 3 and 10, another embodiment of the invention is shown generally at 40 and comprises prosthesis insert 42 and implant insert 50. In this embodiment, the implant insert 50 is threadably engaged by its lower threaded portion into mateing female threads within dental implant DI2 secured within the alveolar bone B. The outer surface 62 of support 52 may include hexagonal flats to facilitate the secure tightening of implant insert 50 within the mating threads of dental insert DI2.

The prosthesis insert 42 is comprised of mating inner and outer threaded coaxial stems 46 and 66, respectively. Inner stem 46 includes spherically shaped clamping shell 48 disposed at its lower end, while outer stem 66 includes spherically shaped clamping shell 44 disposed at its lower end. Disposed at the upper end of implant insert 50 is an integral spherically shaped generally hollow support 52 having an inner and an outer surface. The inner surface of support 52 is adapted to mate against the outer surface of clamping shell 48, while the outer surface of support 52 is adapted to mate against the inner surface of clamping shell 44. By this arrangement, then, the prosthesis insert 42 may be angularly articulated with its longitudinal axis 56 about point of articulation 60 which is defined by the intersection of longitudinal axis 58 of the implant insert 50 and axis 56.

Spherically shaped support 52 includes aperture 64 disposed through its upper end to accommodate the universal articulation of the prosthesis insert 66 about imaginary articulation point 60, providing clearance for inner stem 46 passing therethrough. Once the dental practitioner has determined the proper angular alignment of axis 56 so as to dispose the prosthesis insert 66 at a mid point within dental prosthesis DP, inner and outer stems 46 and 44 may be rotated one to another so as to forceably urge clamping shells 48 and 44 together. By this means, then, sufficient friction force is exerted against both inner and outer surfaces of support 52 so as to immobilize the prosthesis insert 42 with respect to the implant insert 50 and dental prosthesis DP2.

Compression spring 54 is also provided to exert upwardly pressure against inner clamping shell 48 to retain same in position against the inner surface of support 52 during the preliminary adjusting and the universal articulating of prosthesis insert 42 and its longitudinal axis 56 before securing in place.

It should be noted that outer clamping shell 44, as best seen in FIG. 10, is nonsymmetric so as to provide sufficient engagement against the outer surface of support 52 when extreme angular adjustment of axis 56 is required.

Referring now to FIG. 4, another embodiment of the invention shown generally at 70 includes prosthesis insert 71 and implant insert 74. In this embodiment 70, an intermediate spherically shaped member 84 is provided which is lockably engaged for rotation into mating support 78 disposed at the upper end of implant insert 74. The lower end 80 of outer stem 72 of prosthesis insert 71 includes a mating spherically outer shell structure which engages around the outer surface of support 78. The prosthesis insert 71 also includes inner stem 82 which is threadably engageable within outer stem 72 so as to coaxially pass through and threadably engage within a mating thread disposed centrally through intermediate member 84. By this means, then, as previously described with respect to FIG. 2, a drill bit may be passed longitudinally through outer stem 72 and intermediate member 84 to prepare cavity 86 in implant insert 74 once the dental practitioner has determined the proper angular alignment of the prosthesis insert 71. Thereafter, inner stem 72 is threadably engaged into outer stem 72, through intermediate member 84 and into cavity 86 so as to secure the entire arrangement at the predetermined angular relationship required.

Referring now to FIGS. 5 to 7, another embodiment of the invention is shown generally at 90 and includes prosthesis insert assembly 91 and implant insert 94. The implant insert includes enlarged spherically shaped ball 98 disposed at its upper end. The prosthesis insert assembly 91 includes outer stem 92 having a socket 96 disposed at its lower end which is locked and mateably engaged over ball 98 for universal articulation therebetween. Prosthesis insert assembly 91 also includes inner stem 102 having external threads which mateably engage within longitudinal female threads 100 in outer stem 92. Once the dental practitioner, as previously described, has established a proper angular orientation about point of articulation 108 between the longitudinal axis of the prosthesis insert assembly 91 and that of the implant insert 94, inner stem 102 may be tightened and forceably urged against the top surface of ball 98 within socket 96 to establish and secure by friction force this angular relationship. Thereafter, drill bit D may be used to prepare cavity 106 as best seen in FIG. 7 into which locking pin 106 is inserted in alignment and registry with longitudinal aperture 104 in inner stem 102. The entire prosthesis insert assembly 91 is then embedded and encapsulated within a suitably prepared cavity in the dental prosthesis DP, serving to additionally trap locking pin 106 in secure position as shown.

Again, in this embodiment 90, insert implant 94 is shown secured by cementation and/or forced interference fit within dental implant DI4 which, in this instance, is depicted cemented within the root R of a natural tooth.

Referring now to FIGS. 8 and 9, yet another embodiment of the invention is shown generally at 110 and includes prosthesis insert 116, interlocking eye bolts 112, tapered spacer 124 and locking nut 120. Interlocking eye bolts 112 have continuous rings 114 disposed from one end of each, the rings 114 interlocking and contacting when tensioned apart about point of articulation 128.

Lower eye bolt 112 is shown threadably engaged within dental implant DI5, this lower eye bolt 112 thus being equivalent to an implant insert as previously described.

Upper eye bolt 112 is disposed longitudinally within prosthesis insert 116 and held thusly for longitudinal adjustment and tensioning by internally threaded nut 120 which mateably engages within cavity 118 as shown.

Disposed between the prosthesis insert 116 and the dental implant DI5 is tapered spacer 124 having end surfaces 130 and 132 mating respectively thereagainst at an acute angle one to another. Longitudinal aperture 126 is provided to facilitate positioning of the interlocking rings 114 therewithin. In this embodiment, as best seen in FIG. 9, a set of tapered spacers typlified at 124, having diagonally disposed end surfaces typically 130 and 132, are provided at various discrete angles so that the dental practitioner may select the proper spacer 124 to establish the desired angular relationship between the longitudinal axis of the prosthesis insert 116 and implant insert/lower eye bolt 112 about point of articulation 128. Again, this angular relationship is required and dictated by the necessary angular alignment of the dental prosthesis DP in relation to the other adjacent teeth in the patient's mouth.

Once the proper spacer 124 has been positioned around locking ring 114, threaded nut 120, threadably engaged over eye bolt 112, may then be tightenably secured within cavity 118 so as to rigidly compress and stabilize the prosthesis insert 116 ready for installation of the dental prosthesis DP thereover.

Figure 11:
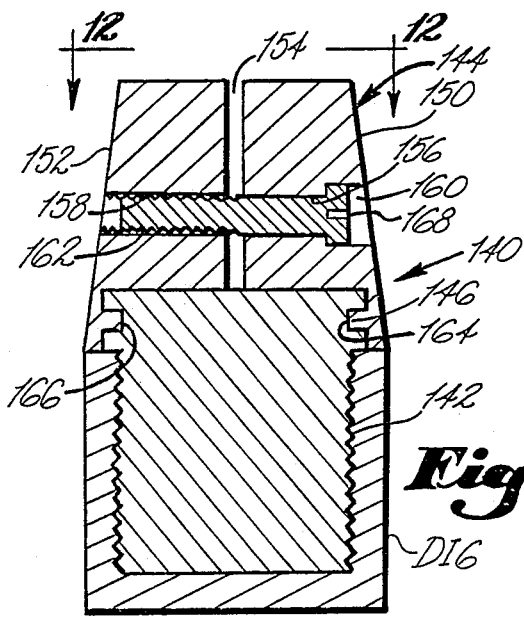
FIG. 11 is a side elevation section view of yet another embodiment of the invention.
Figure 13:
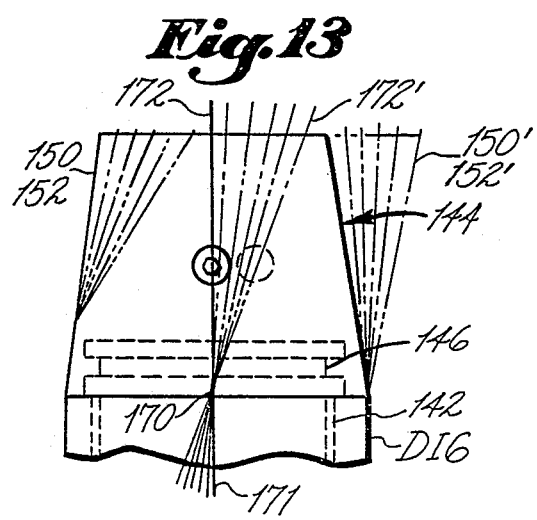
FIG. 13 is a view in the direction of arrows 13—13 in FIG. 12.

Referring now to FIGS. 11 to 13, yet another embodiment of the invention is shown generally at 140. This embodiment 140, although generally providing structure which functions in a similar fashion to the other embodiments of the invention, provides incremental universal adjustment of the prosthesis insert rather than infinite adjustment within a set range.

This embodiment 140 includes an implant insert 142 which is threadably engaged within the dental implant DI6. The upper end of implant insert 142 includes a transverse annular groove 146 positioned adjacent the upper end of the implant insert 142. The prosthesis insert 144 of this embodiment is generally formed of two mating halves 150 and 152 which, when moved together as shown in the figures, mateably engage at 164 and 166 into groove 146 to securely orient the prosthesis insert 144 atop and connected to the implant insert 142. The prosthesis insert halves 150 and 152 are structured so as to provide gap 154 therebetween and securely held in this position and from rotation by threaded cross pin 160 which is disposed transversely within smooth aperture 156 and threaded aperture 158. After securing prosthesis insert 144 atop implant insert 142, as in the previous embodiments, the dental prosthesis (not shown) is connected atop the prosthesis insert 144.

To achieve the incremental universal alignment feature between longitudinal axis 172 of the prosthesis insert 144 and the longitudinal axis 171 of the implant insert 142, the dental practitioner is provided with an array of prosthesis insert halves 150' and 152' as best seen in FIGS. 12 and 13 which collectively provide an incremental array of acute angle axes 172' alignments to axis 171 about the point of articulation 170.

Figure 14:
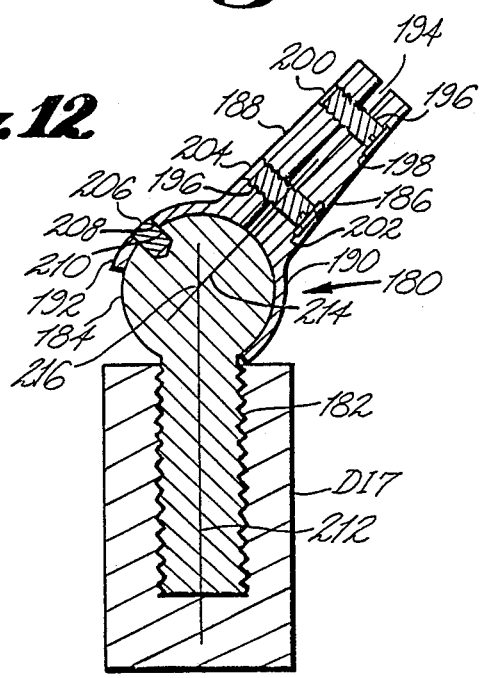
FIG. 14 is a side elevation section view of yet another embodiment of the invention.

Referring now to FIG. 14, a variation of the embodiment of the invention shown in FIGS. 1 and 2 previously described is there shown. This embodiment 180 includes implant insert 182 having its main elongated body externally threaded to mateably engage within female threads provided in dental implant DI7. Integrally disposed at the upper end of implant insert 182 is enlarged ball 184 which mateably engages within the socket formed by the mating socket halves 190 and 192 of the prosthesis insert halves 186 and 188.

As with respect to FIGS. 11 through 13, the prosthesis halves 186 and 188 are held in mateing alignment tightly and securely together by threaded fasteners 196, gap 194 provided between prosthesis insert halves 186 and 188 to insure tightenability of socket halves 190 and 192 against ball 184.

After proper alignment of longitudinal axis 214 in relation to implant insert longitudinal axis 212 about point of articulation 216, threaded fasteners 196 are then tightened and, thereafter to insure immobility of this arrangement, locking pin 206 is forceably urged into cavity 210 in alignment and registry with aperture 208 in socket half 192 as previously described with respect to FIG. 2.

Figure 15:
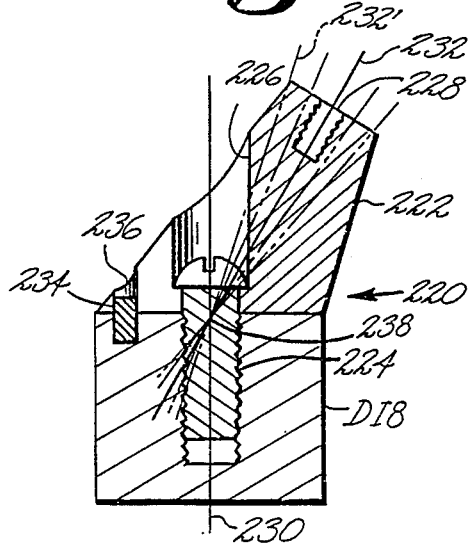
FIG. 15 is a side elevation section view of yet another embodiment of the invention.

Referring lastly to FIG. 15, a variation of the embodiment of the invention shown in FIGS. 11 through 13 is there shown. This embodiment 220 includes a prosthesis insert 222 held in place atop dental implant DI8 by threaded fastener 224 which is threadably engageable into the dental implant DI8. This threaded fastener 224 serves as an implant insert. Aperture 226 is provided in prosthesis insert 222 to securely receive and conceal the enlarged head of threaded fastener 224 as shown.

As with respect to FIGS. 11 to 13, to achieve the incremental universal alignment feature between the longitudinal axis 232 of the prosthesis insert 222 and the longitudinal axis 230 of the implant DI8, the dental practitioner is provided with an array of prosthesis inserts which collectively provide an incremental array of acute angle axes' 232' alignments to axis 230 about the point of articulation 238.

To prevent rotation of prosthesis insert 222 about axis 230, locking pin 234 is provided to be inserted into aperture 236 and the cavity drilled into dental insert DI8 in alignment and registry therewith as previously described.

Threaded aperture 228 is provided in the distal end of prosthesis insert 222 to receive a threaded fastener for assisting in the retention of the dental prosthesis to be applied surrounding the prosthesis insert 222 after it is secured in place.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to entrance any and all equivalent apparatus and articles.

What is claimed is:

1. A universal dental prosthesis retention system for interconnecting a dental implant to a dental prosthesis comprising:
   an implant insert having a first longitudinal axis and securely engageable into the dental implant;
   a prosthesis insert having a second longitudinal axis and securely engageable into the dental prosthesis;
   a universal connector adapted to interconnect said implant insert and said prosthesis insert and adapted to allow said first and second axes to be either colinearly or adjustably moved universally out of alignment to a maximum acute angle one to another about a point of articulation at the intersection of said first and said second axes as defined by said universal;
   means for securely locking said universal connector to maintain a preselected angular alignment between said first and second axes;
   an enlarged ball disposed at the upper end of said implant insert;
   a socket disposed at the lower end of said prosthesis insert; said ball matably and securely trapped within said socket to facilitate said interconnection and said universal articulation;
   said prosthesis insert and said socket are split longitudinally into halves, said halves spaced apart and interconnected by a threaded fastener;
   said threaded fastener adapted to forcibly urge said socket halves against said ball to inhibit relative movement therebetween.

2. A universal dental prosthesis retention system as set forth in claim 1, wherein said locking means also includes:
   a locking screw threadably engaged through the wall of one said socket half and adapted to be rotatably tightened and forceably urged against said ball to further inhibit relative movement therebetween.

3. A universal dental prosthesis retention system for interconnecting a dental implant to a dental prosthesis comprising:
   an implant insert having a first longitudinal axis and securely engageably into the dental implant;
   a prosthesis insert having a second longitudinal axis and securely engageable into the dental prosthesis;
   a universal connector adapted to interconnect said implant insert and said prosthesis insert and adapted to allow said first and second axes to be either colinearly or adjustably moved universally out of alignment to a maximum acute angle one to another about a point of articulation at the intersection of said first and said second axes as defined by said universal;
   means for securely locking said universal connector to maintain a preselected angular alignment between said first and second axes;
   a spherically shaped generally hollow support having an inner and an outer surface and forming the upper end of said implant insert;
   said support having an aperture disposed through its upper end;
   spherically shaped inner and outer clamping shells matably engaged against said support inner and outer surfaces, respectively;

said inner and outer shells having coextensive inner and outer stems radially extending therefrom and forming said prosthesis insert;

said inner stem threadably engageable within, and longitudinally adjustable with respect to, said outer stem and adapted, when rotatably tightened within said outer stem, to forcibly urge said inner and outer clamping shells against said support to inhibit relative movement between said implant and said prosthesis inserts.

4. A universal dental prosthesis retention system as set forth in claim 3, wherein:

said inner stem radially inwardly extends through and is threadably engageable within, a threaded aperture through said inner shell comprising said locking system;

said inner stem further extending into a cavity in said implant insert;

said cavity bored into said implant in alignment and registry with said inner shell threaded aperture and said outer stem after said first and second axes are aligned at a preselected angle one to another.

5. A universal dental prosthesis retention system for interconnecting a dental implant to a dental prosthesis comprising:

an implant insert having a first longitudinal axis and securely engageable into the dental implant;

a prosthesis insert having a second longitudinal axis and securely engageable into the dental prosthesis;

a universal connector adapted to interconnect said implant insert and said prosthesis insert and adapted to allow said first and second axes to be either colinearly or adjustably moved universally out of alignment to a maximum acute angle one to another about a point of articulation at the intersection of said first and said second axes as defined by said universal;

means for securely locking said universal connector to maintain a preselected angular alignment between said first and second axes;

an interlocked pair of rings each having an integral threaded shaft extending radially from each of said pair of rings;

a tapered spacer having a central aperture and having end surfaces which are adapted to matably engage against said prosthesis insert and said implant insert, respectively;

said end surfaces disposing said first and second axes at a preselected angle one to another;

said pair of rings disposed generally within said central aperture;

one said shaft threadably engageable into said implant insert, the other said shaft threadably engageable within said prosthesis insert.

6. A universal dental prosthesis retention system for interconnecting a dental implant to a dental prosthesis comprising:

an implant insert having a first longitudinal axis and securely engageable into the dental implant;

a prosthesis insert having a second longitudinal axis and securely engageable into the dental prosthesis;

a first and second elongated shaft each having a ring disposed from its proximal end, said rings interlocking to allow said first and second axes to be either colinearly aligned or adjustably moved universally out of alignment one to another about a point of articulation at the intersection of said first and second axes;

a tapered spacer having a central aperture adapted to receive said interlocking rings and having end surfaces which are adapted to matably engage against said prosthesis insert and the dental implant to establish and maintain a selected angular alignment between said first and second axes;

said first shaft forming said implant insert, said second shaft securely engageable into said prosthesis insert and adapted to be adjustably positionable along said second longitudinal axis to securely maintain said tapered spacer between and against the dental implant and said prosthesis insert at the preselected angular alignment between said first and second axes established by said tapered spacer end surfaces.

7. A universal dental prosthesis retention system for interconnecting a dental implant to a dental prosthesis comprising:

an implant insert having a first longitudinal axis and securely engagable into the dental implant;

a plurality of prosthesis inserts each having a second longitudinal axis and each securely engagable into the dental prosthesis;

said implant insert also having a transverse groove disposed into its outer surface adjacent its upper end;

each said prosthesis insert split longitudinally into halves, said halves spaced apart and interconnected by a threaded fastener;

each said threaded fastener adapted to be tightened and to forceably and lockably urge said halves together;

each of said prosthesis inserts adapted at their lower ends to be lockably interengageable around and into said groove and to be forceably urged against said implant insert upper end when each said threaded fastener is tightened;

each said prosthesis insert fixedly defining a different said second longitudinal axis and a different predetermined angular alignment between said first and second intersecting axes.

* * * * *